United States Patent [19]

Thorogood

[11] 4,148,884

[45] Apr. 10, 1979

[54] CERTAIN LODOPHOR DISINFECTANT COMPOSITIONS

[76] Inventor: Douglas E. Thorogood, Wingate House, Shaftesbury Ave., London W.C.1, England

[21] Appl. No.: 797,184

[22] Filed: May 16, 1977

Related U.S. Application Data

[63] Continuation of Ser. No. 510,752, Aug. 30, 1974, abandoned, which is a continuation of Ser. No. 272,008, Jul. 14, 1972, abandoned, which is a continuation of Ser. No. 888,926, Dec. 29, 1969, abandoned, which is a continuation-in-part of Ser. No. 854,793, Sep. 2, 1969, abandoned, which is a continuation-in-part of Ser. No. 727,376, May 7, 1968, abandoned, which is a continuation-in-part of Ser. No. 541,517, Apr. 11, 1966, abandoned.

[51] Int. Cl.² ............... A01N 11/00; A61K 33/18

[52] U.S. Cl. .................. 424/150; 424/127; 424/149; 424/177; 424/151; 424/227; 424/271; 424/346; 424/324; 424/334; 252/106; 252/107

[58] Field of Search ............. 424/150, 316, 149, 127, 424/177, 227, 271, 324, 334; 252/106, 107

[56] References Cited

U.S. PATENT DOCUMENTS

| | | | |
|---|---|---|---|
| 3,028,299 | 4/1962 | Winicov et al. | 424/150 |
| 3,196,173 | 7/1965 | Willmund et al. | 424/316 |
| 3,223,704 | 12/1965 | Shibe et al. | 424/316 |

*Primary Examiner*—V. D. Turner

[57] ABSTRACT

Stable microbicidal disinfectant compositions comprising a complex of a halogen, a nonionic surface-active agent, and an -onium salt of an alkyl amine characterized by a negative reaction to standard tests for free halogen, no loss of halogen when boiled in an aqueous solution, and having microbicidal activity.

11 Claims, No Drawings

CERTAIN IODOPHOR DISINFECTANT COMPOSITIONS

CROSS REFERENCE TO RELATED APPLICATIONS

This is a continuation of application Ser. No. 510,752, filed Sept. 30, 1974, now abandoned which in turn is a continuation of Ser. No. 272,008, filed July 14, 1972, now abandoned, which in turn is a continuation of Ser. No. 888,926, filed Dec. 29, 1969, now abandoned, which in turn is a continuation-in-part of Ser. No. 854,793, filed Sept. 2, 1969, now abandoned, which in turn is a continuation-in-part of Ser. No. 727,376, filed May 7, 1968, now abandoned, which in turn is a continuation-in-part of Ser. No. 541,517, filed Apr. 11, 1966, now abandoned.

BACKGROUND THE THE INVENTION

The field of the invention relates to compositions of matter and processes of treatment for disinfecting and for killing or disabling the growth of microbes.

Numerous proposals have been made in the past to provide disinfectant compositions for killing or controlling microorganisms which involved the complexing of iodine with various compounds which have the property of liberating the iodine for its disinfecting properties under conditions of use. These compositions are generally referred to in the art as iodophors, and their disinfectant and germicidal activity is derived essentially from the free iodine which they liberate. Characteristics of these iodophor compositions include their positive reaction to the starch-iodine test and their progressive loss of iodine from aqueous solution. For example, if an aqueous solution of such an iodophor is boiled, all of the iodine is very soon lost by volatilization. The standard iodophors, if extracted with an organic solvent such as chloroform, or carbon tetrachloride give rise to a violet non-aqueous phase which consists of molecular iodine dissolved in the solvent.

It is also known to be possible to make complexes of iodine that may be fairly stable but these complexes of iodine possess reduced, very little or no germicidal or anti-microbial activity.

SUMMARY OF THE INVENTION

The present invention relates to a new class of complexes or compositions broadly composed of a halogen, an -onium alkyl amine salt and a nonionic surface-active agent.

The new class of complexes or composition of matter of this invention are not halogen complexes as commonly known and described. They do not, for example, show the presence of halogens, such as shown by the standard tests therefor, for example the well known starch-iodine test. The complexes do not lose halogen even when boiled in aqueous solutions and on extraction with organic solvents, such as, chloroform and carbon tetrachloride. They give rise to a different non-aqueous phase when extracted with a solvent than with conventional and known iodophors. For example, when iodine is used to form the complexes of this invention, the non-aqueous phase is a yellow-brown color rather than violet. The complexes of this invention nevertheless have disinfectant or anti-microbial activity comparable with that of the known iodophors and in most instances even superior and of low toxicity.

This invention further includes new compositions of matter in which the novel complexes of this invention are used in conjunction or in admixture with other compositions, such as, antibiotics, materials capable of disrupting disulfide linkages, cationic surface-active agents, formaldehyde, and so forth, which significantly enhance the microbicidal activity of the complexes and impart to the complexes a wider range of uses. It is contemplated that most any material can be added to the complexes, due to their excellent stability, so long as the material does not materially affect the stability or the microbicidal action of the complexes.

DESCRIPTION OF PREFERRED EMBODIMENTS

Various salts of alkylamines (hereinafter referred to as alkylamine salts) can be used to form complexes according to this invention in combination with the nonionic surface-active agents and the halogen.

The alkylamine salts that can be used according to this invention are advantageously salts of higher alkylamines such as dodecyl and tetradecyl amine and include for example alkyl sulfonate (advantageously ethane sulfonate), sulfamate, p-amino benzene sulfonate, 4-amino benzoate, acetate, and the nitric acid and hydrochloric acid salts of the alkylamines or mixtures thereof. The alkylamine sulfamate salts wherein the alkyl group contains between 12 to 14 carbon atoms is the most advantageous amine salt used to date.

Various derivatives of the alkylamine salts can also be used, such as, the phenol or aryl modified amine salts hereinafter disclosed. Ethoxylated alkylamine salts can also be used. The exact extent to which the basic alkylamine salts can be modified and still operate according to this invention is not known but this could be determined by routine experimentation by those skilled in the art. The term alkylamine salts as used herein is thus intended to include alkylamine salt derivatives and modifications thereof, such as, the aryl and ethoxylated derivatives hereinafter disclosed.

The alkylamine salts of this invention can be prepared, for example, by reacting long chain alkyl fatty acid amines with a sulfonic acid, sulfamic acid, various amino carboxylic acids, organic acid or inorganic acids such as hydrochloric acid by conventional and well known procedures for forming amine salts. Sulfamic acid has been found to be most advantageous. The alkylamines used to form the alkylamine salts advantageously contain between about 12 to 14 carbon atoms, such as, dodecyl (12 carbon atoms) and tetradecyl (14 carbon atoms), although the number of carbon atoms can vary. For example, an alkylamine salt has been used in which the number of carbon atoms varied from $C_8$ to $C_{18}$ with $C_{12}$ and $C_{14}$ predominating. Mixture of various alkylamines can also be used. The exact range of the number of carbon atoms which can be used for the alkyl group, that is, below 12 or above 14 carbon atoms or the extent of modification thereof, is not known but this could readily be determined by one skilled in the art by routine experimentation. Various derivatives of the higher alkylamines might also be used provided that the derivatives do not interfere with the function of the alkylamine salt in forming the stable microbicidal complex. The number of carbon atoms contained in the alkylamine may also depend on the number of carbon atoms contained in the acid to be reacted with the amine to form the alkylamine salts.

Some example of acids that can be used to react with the alkylamines include sulfamic acid, alkyl sulfonic acids, such as, ethane sulfonic acid, dodecyl amino sulfonic acids, para-amino benzene sulfonic acid, 4-amino benzene carboxylic acid, amino acetic acid (glycine), diglycine, amino alkyl sulfonic acid, and so forth. The exact number of carbon atoms which can be contained in the alkyl or aryl portions of the acids is not known but this could readily be determined by routine experimentation. Experiments to date indicate with the sulfonated amines the chain lengths can generally vary from about 2 to 20 carbon atoms when using an alkylamine containing 12 to 14 carbon atoms. Amines such as coconut dimethylamine, aminoethyl ethanolamine, and stearyl dimethylamine reacted with sulfamic acid are further examples of amine salts that can be used according to the invention. The criteria being that the alkylamine salt when combined with a nonionic surface-active agent and a halogen, such as iodine, must produce a stable composition or complex which gives a negative reaction to the standard tests for determining the presence of the particular halogen employed, stability with little or no halogen loss when boiled in an aqueous solution and having microbicidal disinfectant activity.

Inorganic acids, such as, nitric acid and hydrochloric acid, can also be used according to this invention to form the alkylamine salts. Other inorganic acids might also be used, such as, phosphoric acid. Experiments to date, however, have indicated that the complexes produced using the hydrochloric acid salt of dodecylamine in accordance with this invention are not as stable as those produced with the other acids.

Among the various derivatives alkylamine sulfonates of sulfamates that can be used is included the reaction product of tetraethoxynonyl phenol, glycerol and an alkyl amino sulfonic acid, such as, dodecylamine sulfonic acid. Other alkyl or aryl modified amine sulfonates may be substituted for the above substituted alkylamine sulfonate so long as they possess the necessary properties to produce the halogen or iodine complexes having the microbicidal disinfectant and stability properties disclosed herein. The number of carbon atoms of the aryl radical or alkyl-aryl radical which can be employed, either higher or lower, has not been determined, but this could be determined by routine experimentation.

The inorganic acid salts can be prepared by simple processes as will be apparent to those skilled in the art. The nitric acid salt can be prepared, for example, by dissolving dodecylamine in a small amount of methylated spirit and normal nitric acid added to the dissolved dodecylamine until a pH of about 7 is obtained. The addition of the acid is made with stirring and some frothing may occur. Similarly, the hydrochloric acid salt can be made in the same manner by the addition of normal hydrochloric acid.

The stable, biocidal active agents of this invention can be prepared by adding to the dodecylamine nitric or hydrochloric acid to a solution of a halogen, such as, iodine, and a nonionic surface-active agent as described herein. The complexes thus produced with iodine do not react to the starch-iodine test and have biocidal activity.

The alkylamine sulfonates, sulfamates or carboxylates of this invention can be prepared by known methods, such as, by reacting an alkylamine with a sulfonic acid, or sulfamic acid or an alkyl sulfonic acid.

For example, an alkylamine sulfonate that can be used according to this invention can be prepared by mixing 100 parts of ethyl alcohol with 410 parts of dodecylamine in a suitable vessel and heating the mixture to approximately 50° C. A stream of air is then blown through stabilized sulfur trioxide held at about 80° C. and the resulting gas containing sulphur trioxide passed into the mixture of ethyl alcohol and dodecylamine below the surface thereof. The quantity of sulphur trioxide used is sufficient to supply approximately 1.1 moles of sulphur trioxide per mole of ethyl alcohol. The temperature of the reaction in this particular example should preferably be held under about 55° C. and the reaction mixture agitated for about one hour to complete the reaction. The product is then neutralized with a suitable base, such as, ammonia, ethyl amine or ethanol amine, to form the corresponding salt. The product produced from this process is probably a mixture of products, but nonetheless quite suitable for the purpose of this invention for complexing halogens in conjunction with the nonionic surface-active agent.

A more purified higher alkylamine sulfonate which is also useful in accordance with this invention can be made by mixing 240 parts of dodecylamine in a suitable vessel equipped with a stirrer, and the temperature raised to about 40° C. 100 parts of ethane sulfonic acid are then slowly added and the temperature preferably kept below about 50° C. during the reaction. The reaction mixture is stirred for approximately one hour to complete the reaction.

The dodecylamine sulfamic acid salt can be produced in a similar manner as described above, substituting sulfamic acid for the ethane sulfonic acid as will be apparent to those skilled in the art.

A modified or a derivative of an alkylamine sulfonate can also be prepared by processes well known in the art. One advantageous method of preparing a derivative of an alkylamine sulfonate involves placing 800 parts of tetraethoxynonyl phenol and 100 parts of glycerol in a suitable vessel and efficiently stirring the mixture together. The temperature of the mixture is raised to 90° C. Nitrogen is then blown into the reaction vessel and when substantially all of the air has been displaced, an alkylamine sulfonic acid, typically dodecylamine ethane sulfonic acid, is slowly added thereto over a period of 3 hours. The quantity added should be sufficient to supply approximately 1.1 moles of the amine sulfonic acid per mole of tetraethoxynonyl phenol. The reaction mixture is finally agitated at a temperature of about 115° C. for 1 hour. Using this particular process, the nonyl phenol amine sulfonate is obtained directly in the form of the ammonium salt due to the use of the amine sulfonic acid as the sulfonating agent.

The other alkylamine salts described above can be prepared in similar manners as known to those skilled in the art.

The various alkylamine sulfonates discussed above may be used as such or as salts, e.g., sodium, potassium or ammonium salts.

The halogens that can be used to form the novel complexes of this invention include iodine, bromine, chlorine and interhalogen compounds of iodine, bromine or chlorine, such as iodine chlorine, iodine trichloride, iodine bromide etc. The interhalogens can also include fluorine. The properties of the various end complexes produced in accordance with this invention will of course vary depending upon the particular halogen or interhalogen employed.

Various well-known nonionic surface-active agents can be used in conjunction with the alkylamine sulfonates and the halogens to form the stable complex of this invention. To date, no nonionic surface-active agent has been found which cannot be used to form the new class of disinfectant compositions according to this invention. The particular nonionic surface-active agent used will depend upon or be dictated by the intended use of the complexes and properties desired, such as, viscosity, miscibility, toxicity, temperature, stability, costs, and so forth.

Examples of the more advantageous nonionic surface-active agents, which may be characterized as complexing aids, include the nonionic ethylene oxide condensate-type surface-active agents, such as, the polyethoxylates of alkyl phenols in which the alkyl group contains from about 7 to 11 carbon atoms and the condensate contains about 9 to 17 ethylene oxide units. Dimethylnonyl polyethoxylate, marketed under the name Tergitol 15-S-9 by the Carbide and Carbon Chemicals Co., has been found to be particularly advantageous. The numeral 9 indicates the presence of 9 ethylene oxide units, but it is understood that many more ethylene oxide units can be present, even up to 20 to 30 ethylene oxide units. Some examples of nonionic surface-active agents which might be used are described in Brost et al. U.S. Pat. No. 2,989,434.

Further examples of nonionic surface-active agents which can be used in conjunction with the alkylamine acid compounds are the nonionic betaines, such as, the N-alkyl betaines, for example, N-lauryl betaine, nonyl phenyl ethers of polyethylene glycol, polypropoxypolyethoxy glycol, tridecyl polyethoxyethanol, polyethylene glycol monolaurate, and polyoxy ethylated monolaurate. It is advantageous to use betaines in which the alkyl group is of higher molecular weight, for example, those containing 9 to 14 carbon atoms.

It is particularly advantageous to use higher molecular weight nonionic ethylene oxide condensation products containing 9 or more moles of ethylene oxide since it has been found that this results in a novel complex which is less irritating and less toxic particularly when the complex is to be used for oral administration to animals.

Although the exact mechanism is not known, it is quite clear that the nonionic surface-active agents, the alkyl or aryl-alkyl modified amine salt compounds and the halogen actually enter into a molecular structure resulting in stable halogen complex and become an integral part thereof. Accordingly, the precise nature of the stable complex which is formed will depend in part upon the particular nature and type of nonionic surface-active agent employed, together with the alkyl or aryl-alkyl modified amine salts and halogen used to form the complex.

The production of the novel complexes of this invention is particularly simple. All that is required is to mix the three components together, namely, the alkylamine salt; such as, an alkylamine sulfamate, the nonionic surface-active agent, and the halogen, and maintain them at a moderately elevated temperature with agitation. The purpose of the agitation is merely to insure that the reagents are kept in intimate contact with each other during the formation of the complex.

The proportions of the alkylamine salts, the nonionic surface-active agent, and the halogen are not critical although the reaction proportions appear to be specific since any excess halogen generally will remain separate. Iodine, for example, will remain at the bottom of the reaction vessel or distill depending on the reaction temperature while any excess alkylamine salt will generally remain as a separate phase at the top of the reaction mixture. Any excess nonionic surface-active agent appears to remain as a diluent in the reaction mixture without adversely affecting the formation or properties of the novel anti-microbial complexes. Excess nonionic agents may at times be advantageous, depending on the viscosity and use desired. An example of specific proportions which can be used as a guide where the nonionic surface-active agent is nonyl phenol polyethoxylate, such as, the sodium salt, is one part of halogen, such as, iodine, 2½ parts of the alkylamine sulfamate or the alkylamine alkyl sulfonate produced according to the procedure described above using sulphur trioxide to form the sulfonate (preferably 5 parts in the form of a 50 percent aqueous dispersion of solution) and 9 parts of the nonyl phenol polyethoxylate. With these proportions the iodine and the alkylamine salts are substantially completely complexed together with the nonyl phenol polyethoxylate and a minimum of the nonyl phenol polyethoxylate is left as a diluent in the final product. It is understood, however, that these proportions will vary depending upon the particular alkyl or alkyl modified amine salt, sulfonate or sulfamate and nonionic surface-active agent used. When using other halogens these proportions may be altered, depending upon the molecular weight of the halogen.

The preferred procedure for making the novel complexes is first to mix the alkylamine salt and the nonionic surface-active agent in a suitable vessel furnished with heating and stirring means and heating the mixture to about 70° C. to 75° C. while stirring until a clear solution results, after which the halogen, such as, iodine, is charged in the vessel and agitation continued for a sufficient time to insure dissolution. The halogen can also be added to the amine salt such as the amine sulfamate salt and the nonionic agent later added. Usually approximately 30 minutes will be required to complete the complexing reaction, but this will vary to some extent depending upon the nature of the agitation, the temperatures used, as well as the specific ingredients employed in making the complexes. It is generally advantageous to maintain the reactions temperature as low as practical. Generally, continued agitation, even for several hours, will not have any adverse effects in the production of the complexes. After the reaction has been completed, the mixture is allowed to cool if heat is employed. The end product may be diluted with water, preferably distilled or demineralized water, to a standard or desired concentration, depending upon the end use desired of the product. Any addition of water, whether it be for the purpose of diluting to a predetermined desired concentration or merely for the purpose of making good water loss during the reaction, should be deferred until the reaction is complete.

The novel complexes of this invention are in general semi-solid or viscous liquids and their color, odor, and taste will depend on the particular halogen employed. Where iodine is employed, the complexes generally have a deep yellowish-brown color. They are in general heavier than water; they show no reaction for free halogen at room temperature or at up to 100° C.; they show no loss of iodine on heating up to 100° C. in water and in general no loss on heating up to 200° C. in a solvent other than water. The complexes are non-irritating and have a very low toxicity, permitting oral administration to animals.

Mixtures of various different alkyl or alkyl-modified amine salts as well as mixtures of various different non-ionic surface-active agents can be used in accordance with this invention. Mixtures of the various halogens or inter-halogens could also be used if desired.

As previously discussed, the novel halogen complexes of this invention have the same or better microbicidal disinfectant or germicidal properties as the known iodophors and can be used in the same manner. The novel complexes of this invention can further be diluted with water and are effective for controlling or killing against both gram-negative and gram-positive organisms, spores, fungi, nematodes eggs, and viruses. They have the advantage that the halogens, such as, iodine, can be fully complexed and are thus rendered stable, non-irritating, and nontainting and still retain their microbicidal activity. The novel compositions are less staining than the common iodophors in relation to any materials, such as, cotton and nylon fabrics. Further it becomes possible to use numerous and other additives, such as, perfumes, previously unstable in the presence of a simple iodine solution or common iodophors.

The novel complexes of this invention can be applied in known manners for the purpose of disinfecting hospitals, animal living quarters; such as, stalls, pens, kennels, etc. This type of use is best affected by diluting the complex with a suitable amount of water and discharging it through a conventional aerosol container.

The complexes of this invention can also be used for topical application to animals and humans at the concentration required or desired by incorporating it into suitable and known carriers to form solutions or creams so long as the carrier does not adversely affect the disinfectant properties or the stability of the complex. The complexes can also be used in admixture with various soaps and shampoos and on bandages or gauze for a wound or sanitary dressing.

The complexes of this invention can also be used orally and fed to animals and birds or administered by injection. Oral use can be best accomplished by adsorbing the complex onto a suitable powder, such as, silica powder, and mixing with the animal feed. It can also be given to animals by incorporation into drinking water. The complexes have been adsorbed onto silica powder and mixed with animal feed and fed to chickens, turkeys, and pigs without any noticeable toxic effects.

The $LD_{50}$ of the halogen complexes produced according to this invention is very low and is generally better than about 5.3 gms. per kilo in albino mice.

The complexes of this invention also retain their activity even when contaminated with organic matter and show significant improvement over commercially available iodophors.

The following examples illustrate the preparation of compositions in accordance with the invention:

EXAMPLE 1

12 parts by weight of monopropylene glycol; 26 parts by weight of dodecylamine sulfamate (ammonium salt) and 50 parts by weight of dimethylnonyl polyethoxylate (Na salt) containing approximately 9 ethylene oxide units (Tergitol 15-S-9) are placed into an externally water heated reactor and the temperature of the water is raised to boiling and the contents of the reaction vessel stirred. The temperature of the contents of the reaction vessel becomes steady at about 97° C. at which time they become clear and homogeneous.

12 parts by weight of iodine in granular form is then added to the reaction mixture. The temperature of the reaction mixture rises between about 10° and 15° C. after the addition of the iodine, but there is little or no loss of iodine. The reactants are then stirred for an additional 30 minutes, the heat removed, and the complex recovered. The resulting complex is stable and shows no reaction to the standard starch-iodine test. The complex posseses disinfectant and microbicidal properties and when extracted with chloroform gives rise to a yellow-brown non-aqueous phase. The complex when mixed with water and boiled shows insignificant or no loss of iodine.

EXAMPLE 2

100 parts by weight of monopropylene glycol, 215 parts by weight of dodecylamine sulfamate (ammonium salt) in a finely powdered form, 60 parts by weight of an ethoxylated dodecylamine sulfamate anhydrous alcohol paste (50 percent solids) and 360 parts by weight of Tergitol 15-S-9 (as previously described) are mixed together and heated in the same manner as described in the above example. The iodine in granular form is then added to the reaction mixture and the temperature of the reactants rises about 10° to 15° C. with little or no loss of iodine. The reactants are stirred for 30 minutes, the heat removed and the complex recovered from the reaction vessel. The complex has properties very similar to those described with respect to the complex prepared in accordance with the previous example.

EXAMPLE 3

100 parts by weight of monopropylene glycol, 215 parts by weight of dodecylamine sulfamate (ammonium salt) in a finely powdered form, 60 parts by weight of an ethoxylated dodecylamine sulfamate anhydrous alcohol paste (50 percent solids) and 360 parts by weight of Tergitol 15-S-9 (as previously described) are inserted into a glass reaction, fitted with a stirrer, condenser and tap funnel. 65 parts by weight of bromine is then weighed into the tap funnel and the reaction flask placed in a water bath at 25° C. The reactants are stirred vigorously and the bromine added slowly from the tap funnel over a period of 10 minutes. The temperature of the reactants rise about 2° C. During the whole time of addition of the bromine, no signs of bromine vapor are observed in the condenser.

The reaction mixture at this point is a golden-brown suspension. Heat is then applied to the water bath at such a rate as to give a steady rise in temperature at a rate of about 1° C. every 1½ minutes up to a temperature of 80° C. There is at no time any violent or vigorous reaction and as the temperature rises above 75° C. the mixture becomes clear and homogeneous and is golden-orange in color. There is no smell of free bromine. A small portion of the bromine complex of this invention was dissolved in water and treated with potassium iodide and starch. No positive reaction was obtained. The bromine complex so produced gives a clear aqueous solution, it is heat stable and possess disinfectant and anti-microbial activity.

The chlorine or interhalogen complexes of this invention can be produced in a similar manner as described above as will be apparent to those skilled in the art.

EXAMPLE 4

5 parts of a 50 percent suspension or solution of alkylamine sulfonate produced according to the example described above using sulphur trioxide to form the sulfonate are mixed with 9 parts of nonyl phenol polyethoxylate (Na salt) and are heated to 70°–75° C. with stirring until the solution becomes clear. One part of iodine is then added to the clear solution and agitation continued for about 30 minutes until substantially complete dissolution of the iodine and the complexing of the reactants is completed. The complex is then cooled and can be diluted with distilled water to the concentration desired. Parts are by weight, taking iodine as 1. The above disinfectant composition was tested and found successful for the controlling and killing of numerous micoorganisms, including *Pseudomonas pyocyanea*, Staphlococcus strains, as well as various fungi and viruses.

EXAMPLE 5

4.1 parts by weight of an alkylamine sulfonate ($NH_3$ salt) prepared according to the process disclosed above using sulphur trioxide to form the sulfonate is thoroughly mixed with 3.6 parts by weight of n-octyl phenol ethylene oxide condensate containing 9 moles of ethylene oxide and heated to about 75° C. until a clear solution results. One part by weight of iodine is added thereto with continued heating and stirring until the complex reaction is completed (approximately 30 minutes). The complex is cooled and possessed substantially the same disinfectant properties as the complex of Example 4.

EXAMPLE 6

0.5% iodine
5% ammoniium salt of N-lauryl (amino sulfonic) beta-amino butyric acid
5% N-lauryl betaine
5% isopropyl alcohol to
100% water (distilled)

EXAMPLE 7

2% iodine
15% sodium salt of N-lauryl (amino sulfonic) beta-amino butyric acid
20% N-lauryl betaine
20% isopropyl alcohol to
100% water (distilled)

EXAMPLE 8

8% iodine
40% ammonium salt of N-lauryl (amino sulfonic) beta-amino butyric acid
30% N-lauryl betaine to
100% isopropyl alcohol N-lauryl tetraethoxy amino sulfonic acid can be used in place of the N-lauryl (amino sulfonic) beta-amino butyric acid in Examples 6–8.

The formation of the compositions of this invention can form by using a glycol, such as, ethylene glycol, a lower monoalcohol such as methanol or isopropyl alcohol or an N-alkyl betaine in the reaction. Other materials can also be used provided they do not interfere with the formation of the novel complexes of this invention as will be apparent to those skilled in the art.

The other halogens, such as, chlorine, and bromine also have germicidal activity. In forming the complexes with the other halogens or interhalogens it is advantageous to employ approximately stoicheometric amounts and therefore approximately the same number of moles of the other halogens or interhalogens should be used above with respect to iodine. Different temperatures or pressure may have to be employed when using other halogens or interhalogens as will be apparent to those skilled in the art.

The pH of the complexes or solutions thereof of this invention is preferably retained on the acid side, but the invention is not limited thereto. The pH will depend on the end use desired of the product as well as the pressure or absence of materials in admixture therewith. It is generally advisable to maintain the pH below about 7 and preferably 6. In some instances the pH can be higher or lower and at times can be fairly alkaline, depending on the particular materials used to form the complex and the particular materials used in conjunction therewith or additives for the complex. The pH of the aqueous solutions of the complexes of this invention can be adjusted by the addition of compatible alkaline agents, such as, sodium hydroxide or acidic agents, such as, sulfamic acid so long as they do not disrupt or interfere with the stability or biocidal activity of the complexes.

The microbicidal complexes of this invention can advantageously be used in combination or in admixture with other materials which will enhance the microbicidal activity or act synergistically therewith.

It has been found, for example, that the addition of small amounts of cationic active surface-active agents act synergistically with the complexes of this invention and enhance the microbicidal activity thereof. Most any of the cationic surface-active agents can be used to accomplish this result, such as, alkyl dimethyl benzyl ammonium chlorides, so long as they do not disrupt the stability of the complex. Small amounts of anionic agents such as sodium dodecyl benzene sulfonate can be added but present evidence shows a depression in activity at high concentrations. Addition of non-ionic agents can also be added to the complexes or compounds of this invention, such as an ethylene oxide (9 moles) condensate of octylphenol.

The addition of antibiotics to the complex of this invention also act synergistically and enhance the microbicidal properties many times more than would be expected. Some examples of antibiotics that have been found to enhance the microbicidal properties include polymyxin, chlorotetracycline, oxytetracycline, chloramphenicol and penicillin G.

The use of the complexes of this invention in combination with or in admixture with disulfide linkage disruption materials or compounds are particularly advantageous for use as a sporicide. Examples of disulfide linkage disruption compounds that can be used in admixture with the complexes of this invention include nitric acid, chelating agents such as ethylene diamine tetra-acetic acid (EDTA), diethylene triamine penta-acetic cyclohexane 1,2 diaminotetra-acetic acid, ethylene glycol bis (aminoethyl) tetra-acetic acid, N-(2 hydroxyethyl) ethylene diamine-N-N',N'-triacetic acid, N,N-di(2 hydroxyethyl glycine sodium salt, ethylene diamine, N,N'-bis (o-hydroxy phenyl acetic acid, and hydrogen peroxide.

The amounts of such additives that can be used can vary quite widely, depending on the end use of properties desired and can be determined by those skilled in the art by routine experimentation. Formaldehyde, for example, can be added as a 1 percent formaldehyde aqueous solution to the complex of this invention diluted to a 10 percent v/v concentration. The complex, for example, can be mixed with the polymyxin B (1 unit per mole) at a concentration of 75 micrograms per mole of the polymyxin. Some other concentrations of additives that can be used are given below in the examples.

The following examples illustrate some various mixtures that can be prepared using the novel microbicidal compositions of this invention:

EXAMPLE 9

A complex was formed by reacting the following compounds as described above

|  | % by weight |
|---|---|
| Monopropylene glycol | 1.2 |
| Dodecylamine sulfamate | 2.6 |
| Tergitol 15-S-9 (as defined above) | 10 |
| Iodine | 1.2 |
| and the following compounds added thereto | |
| Normal nitric acid | 20 |
| Isopropyl alcohol | 10 |
| Demineralized water | 55 |

EXAMPLE 10

|  | % by weight |
|---|---|
| Iodine complex of Example 1 | 15 |
| Tergitol 15-S-9 (as described above) | 7.5 |
| Isopropyl alcohol | 10 |
| Sulfamic acid | 3 |
| Dodecylamine sulfamate | 3 |
| Normal nitric acid | |
| Water, to | 100ml |

EXAMPLE 11

Iodine complex of Example 1 (25% w/v) was buffered to a pH of 7.5 with 3 percent disodium salt of ethylene diamine tetra-acetic acid (EDTA) and N/1 sodium hydroxide. A 10 percent v/v solution was prepared by diluting 10 ml. of the solution with 100 ml of distilled water. The pH of the solution was 7.0. The solution was carefully mixed and held at room temperature (22° C.) for 6 hours. Part of the solution was tested for free iodine with starch with negative results.

EXAMPLE 12

|  | % by weight |
|---|---|
| Hydrogen peroxide 35%/w/w | 10 |
| Tergitol 15-S-9 (as described above) | 11 |
| Isopropanol | 17 |
| Iodine complex (Example 1) | 2 |
| Sulfamic acid | 0.625 |
| Alkyl dimethyl benzyl ammonium chloride 50%/w/w | 2.0 |
| Water to | 100 ml. |

The addition of HI to the compositions of this invention has also been found to be advantageous. The addition of HI to the compositions adds increased stability thereto. The amount of HI added can be varied as will be apparent to those skilled in the art, but it is advantageous to add only a small amount such as about 3.33 percent by weight of the ingredients forming the complex or the 4 ml of 55 percent active HI (in water) as set forth in the following example.

EXAMPLE 13

67 grams of Tergitol 15-S-9 (as described above) was charged into a round bottom flask and heated to 65° C. 5 mls. of isopropanol were then added to the flask and 17.13 grams of dodecylamine sulfamate (finely ground) together with an additional 5 mls. of isopropanol and the reaction mixture stirred. After all of the materials were dissolved, 4 mls. of a 55 percent active HI (ANALAR) were added and the heating of the mixture continued for 20 minutes. 8 grams of iodine were then added thereto and the reaction mixture stirred until the iodine dissolved which took about 30 minutes. 200 mls. of distilled water are then added thereto.

To 3.02 percent by weight of the above composition 2 percent by weight of ethyl dimethyl benzyl ammonium chloride and 0.625 percent by weight of sulfamic acid dissolved in a small amount of water were added thereto. A small amount of acid sodium pyrophosphate dissolved in a little water was then added to the mixture together with approximately 17 percent by weight methanol. 10 percent by weight hydrogen peroxide was then carefully added to the mixture and approximately 56 percent by weight of distilled watter then added and the mixture stirred for 30 minutes.

The above composition was found to be very stable and possessed microbicidal disinfectant and sporicidal properties.

EXAMPLE 14

A composition was prepared in the same manner as set forth in Example 13 using the following ingredients in percent by weight:

|  |  |
|---|---|
| III | 3.33 |
| Methanol | 4.64 |
| Dodecyl amine | 11.43 |
| Sulfamic acid | 5.70 |
| Tergitol 15-S-9 | 66.93 |
| $I_2$ | 7.97 |

The following composition was then prepared (percent by weight) in the same manner as in Example 14

|  |  |
|---|---|
| Complex of Example 14 | 3.02 |
| $H_2O_2$ | 10 |
| Tergitol 15-S-9 | 11 |
| $NH_2SO_3$ | 0.625 |
| alkyl dimethyl benzyl ammonium chloride | 2.0 |
| Water | 56.355 |
| Methanol | 17 |

The uses of the quaternary ammonium compounds in the compositions containing $H_2O_2$ has been found to be particularly advantageous resulting in a significant (synergistic) improvement in activity.

Various amounts of $H_2O_2$ can be used so long as it does not disrupt the stability or activity of the complex. It is advantageous to use an excess to add additional shelf life.

The sodium pyrophosphate is used to impart further stability to the $H_2O_2$ although other known $H_2O_2$ stabilizing agents can be used and in amounts known to the art.

The above compositions produced according to Examples 9 through 14 have very effective microbicidal properties and are particularly effective sporicides. It is advantageous to maintain the pH of the compositions, particularly that of Examples 12 and 13, on the acid side between about 4 to 5½.

The stable complexes of this invention can be tested for microbicidal properties by numerous testing procedures well known to those skilled in the art.

I claim:

1. A bactericidal composition comprising a bactericidal amount of a complex formed by mixing at a reactive temperature in a manner to cause intimate contact of the reactant with each other a reactive amount of a salt of an alkylamine, wherein the alkyl group contains between 8 and 18 carbon atoms, with a reactive amount of a nonionic surface active agent and with a bactericidal amount of a halogen which is iodine, bromine, chlorine or an interhalogen or iodine, bromine, fluorine, or chlorine, said complex characterized by
  (1) a negative reaction to standard starch iodine test for free halogen,
  (2) stability or no loss of halogen when boiled in an aqueous solution, and
  (3) having bactericidal activity.

2. The composition of claim 1 in which the halogen is iodine.

3. The composition of claim 2 in which the salt of the alkylamine is a salt of an organic acid.

4. The composition of claim 2 in which the salt of the alkylamine is a salt of an inorganic acid.

5. The composition according to claim 2 in which the salt of the alkylamine is an alkylamine sulfonate.

6. The composition according to claim 2 in which the salt of the alkylamine is an alkylamine sulfamate.

7. The composition of claim 5 in which the alkylamine sulfonate contains an average of between about 12 to 14 carbon atoms.

8. The composition of claim 1 in which the nonionic surface-active agent is an ethylene oxide condensation product.

9. The composition of claim 8 in which the condensation product contains between about 9 and 17 ethylene oxide units.

10. The composition of claim 2 in which further admixed therewith is a microbicidal amount of polymyxin, chlorotetracycline, oxytetracycline, chloramphenicol or penicillin.

11. The composition of claim 1 in which further admixed therewith is a microbicidal amount of formaldehyde.

* * * * *

UNITED STATES PATENT AND TRADEMARK OFFICE
CERTIFICATE OF CORRECTION

PATENT NO. : 4,148,884
DATED : April 10, 1979
INVENTOR(S) : Douglas Edward Thorogood It is certified that error appears in the above-identified patent and that said Letters Patent are hereby corrected as shown below:

Column 11, line 35, under the heading "% by weight" and adjacent

"normal nitric acid" insert --5ml--

Column 12, line 37, change "III" to

--HI--

Column 13, line 17, change "or iodine" to

--of iodine--

Signed and Sealed this

Tenth Day of July 1979

[SEAL]

Attest:

Attesting Officer

LUTRELLE F. PARKER
*Acting Commissioner of Patents and Trademarks*